United States Patent
Moshos et al.

(10) Patent No.: US 10,035,774 B2
(45) Date of Patent: Jul. 31, 2018

(54) PYRAZOLYL CARBOXYLIC ACID AND PYRAZOLYL UREA DERIVATIVE COMPOUNDS

(71) Applicant: Merck Sharp & Dohme Corp., Rahway, NJ (US)

(72) Inventors: Kristos Adrian Moshos, Belmont, MA (US); Valdas Jurkauskas, Cambridge, MA (US); Yisheng Yang, Shanghai (CN); Youchu Wang, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/536,555

(22) PCT Filed: Dec. 18, 2015

(86) PCT No.: PCT/CN2015/097934
§ 371 (c)(1),
(2) Date: Jun. 15, 2017

(87) PCT Pub. No.: WO2016/095860
PCT Pub. Date: Jun. 23, 2016

(65) Prior Publication Data
US 2017/0362183 A1 Dec. 21, 2017

Related U.S. Application Data

(60) Provisional application No. 62/093,777, filed on Dec. 18, 2014.

(51) Int. Cl.
*C07D 231/40* (2006.01)
(52) U.S. Cl.
CPC ................. *C07D 231/40* (2013.01)

(58) Field of Classification Search
CPC ..................................................... C07D 231/40
USPC ..................... 548/371.4, 371.7, 374.1, 372.5
See application file for complete search history.

(56) References Cited

U.S. PATENT DOCUMENTS

| | | |
|---|---|---|
| 7,129,232 B2 | 10/2006 | Ohki et al. |
| 2016/0176897 A1 | 6/2016 | Moshos et al. |
| 2017/0129906 A1 | 5/2017 | Moshos et al. |

FOREIGN PATENT DOCUMENTS

| | | |
|---|---|---|
| EP | 1556389 | 3/2005 |
| WO | 2005027909 A1 | 3/2005 |
| WO | 2014152763 A1 | 9/2014 |
| WO | WO2016025813 | 2/2016 |
| WO | WO2016025839 | 2/2016 |
| WO | WO2016100897 | 6/2016 |
| WO | WO2016109259 | 7/2016 |

OTHER PUBLICATIONS

Ayoko Toda, et al., Synthesis and SAR of novel parenteral antipseudonmonal cephalosporins: Discovery of FR 264205, Bioorganic and Medicinal Chemistry Letters, 2008, pp. 4849-4852, vol. 18, WO.
PCT International Search Report and Written Opinion for PCT/CN2015/097934 completed on Mar. 17, 2016, dated Mar. 23, 2016; 12 pages.

*Primary Examiner* — Matthew P Coughlin
*Assistant Examiner* — Sagar Patel
(74) *Attorney, Agent, or Firm* — J. Eric Thies; John C. Todaro

(57) ABSTRACT

Pyrazolyl carboxylic acid and pyrazolyl urea derivatives have been synthesized, which are useful in the manufacture of cephalosporin antibiotic compounds.

11 Claims, 2 Drawing Sheets

*Biorg. Med. Chem. Lett.* 18 (2008) 4849-4852

PYRAZOLYL CARBOXYLIC ACID AND PYRAZOLYL UREA DERIVATIVE COMPOUNDS

CROSS REFERENCE TO RELATED APPLICATIONS

This application is a U.S. National Phase application under 35 U.S.C. § 371 of PCT Application No. PCT/CN2015/097934, filed Dec. 18, 2015, which claims priority from PCT Application No. U.S. 62/093,777, Dec. 18, 2014.

TECHNICAL FIELD

This disclosure relates to the synthesis of chemical compounds, including intermediates such as pyrazolyl carboxylic acid and pyrazolyl urea derivatives useful in the manufacture of cephalosporins such as ceftolozane.

BACKGROUND

Ceftolozane is a cephalosporin antibacterial agent of the beta-lactam class (β-lactams), also referred to as CXA-101, FR264205, or by chemical names such as (6R,7R)-5-thia-1-azabicyclo[4.2.0]oct-2-ene-carboxylic acid, 3-[[4-[[[(2-aminoethyl)amino]carbamoyl]amino]-2,3-dihydro-3-imino-2-methyl-1H-pyrazol-1-yl]methyl]-7-[[(2Z)-2-(5-amino-1,2,4-thiadiazol-3-yl)-2-[(1-carboxy-1-methylethoxy)imino]acetyl]amino]-8-oxo; or (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane sulfate is a pharmaceutically acceptable ceftolozane salt of formula (VI) that can be formulated for intravenous administration or infusion.

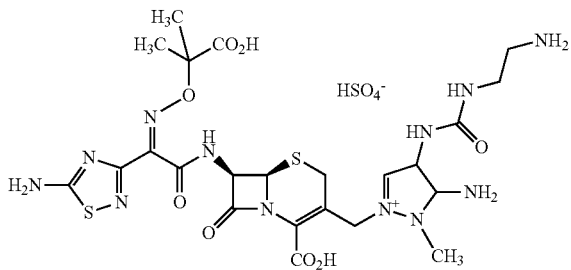

(VI)

Ceftolozane sulfate is also referred to as: 1H-Pyrazolium, 5-amino-4-[[[(2-aminoethyl)amino]carbonyl]amino]-2-[[[(6R,7R)-7-[[(2Z)-2-(5-amino-1,2,4-thiadiazol-3-yl)-2-[(1-carboxy-1-methylethoxy)imino]acetyl]amino]-2-carboxy-8-oxo-5-thia-1-azabicyclo[4.2.0]oct-2-en-3-yl]methyl]-1-methyl-,sulfate (1:1); or 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate. Ceftolozane can be obtained as disclosed in U.S. Pat. No. 7,129,232 and in Toda et al., "Synthesis and SAR of novel parenteral anti-pseudomonal cephalosporins: Discovery of FR264205," *Bioorganic & Medicinal Chemistry Letters*, 18, 4849-4852 (2008), incorporated herein by reference. The antibacterial activity of ceftolozane is believed to result from its interaction with penicillin binding proteins (PBPs) to inhibit the biosynthesis of the bacterial cell wall which acts to stop bacterial replication.

Referring to FIG. 1, synthesis of ceftolozane can be performed via activation of the thiadiazolyl-oximinoacetic acid derivative (I) with methanesulfonyl chloride and $K_2CO_3$ in DMA at 10° C., followed by coupling with the 7-aminocephem (II) by means of $Et_3N$ in cold $EtOAc/H_2O$, affords amide (III). See U.S. Pat. Nos. 7,129,232 and 7,192,943, as well as Toda et al., "Synthesis and SAR of novel parenteral anti-pseudomonal cephalosporins: Discovery of FR264205," *Bioorganic & Medicinal Chemistry Letters*, 18, 4849-4852 (2008). Substitution of the allylic chloride of compound (III) with 4-[(N-Boc-aminoethyl)carbamoylamino]-1-methyl-5-tritylaminopyrazole (IV) in the presence of 1,3-bis(trimethylsilyl)urea (BSU) and KI in DMF then affords the protected pyrazolium adduct (V), which, after full deprotection with trifluoroacetic acid in anisole/$CH_2Cl_2$, can be isolated as the hydrogensulfate salt by treatment with $H_2SO_4$ in i-PrOH/$H_2O$.

The pyrazolyl urea intermediate compound (IV) of FIG. 1 can be prepared from compound (VII) through a sequence of five steps, including one transition metal-catalyzed hydrogenation, as depicted in FIG. 2. Treatment of 5-amino-1-methylpyrazole (VII) with $NaNO_2/HCl$ in water at 5° C. gives the 4-nitrosopyrazole derivative (VIII), which can be reduced to the diaminopyrazole (IX) by catalytic hydrogenation over Pd/C in the presence of $H_2SO_4$. Selective acylation of the 4-amino group of compound (IX) with phenyl chloroformate in the presence of NaOH in $H_2O$/dioxane at 10° C. then yields the phenyl carbamate (X). After protection of the free amine group of carbamate (X) with chlorotriphenylmethane in the presence of $Et_3N$ in THF, the resulting N-trityl derivative (XI) can be coupled with N-Boc-ethylenediamine in the presence of $Et_3N$ in DMF to afford pyrazolyl urea (IV). There is a need for methods of preparing compound (IV) having fewer steps and avoiding the use of transition metal catalysts. There is also a need for chemical intermediates useful in such methods.

SUMMARY

It has now been discovered that a compound of formula (XIV'), e.g., compound (XIV), can be prepared according to the method depicted in FIG. 4 and described herein as Method 1, and that a compound of formula (IV'), e.g., pyrazolyl urea compound (IV), may be prepared from a compound of formula (XIV'), e.g., compound (XIV), according to the method depicted in FIG. 3 and described herein as Method 2. Methods 1 and 2 proceed in good yield. These methods of making compounds of formulas (XIV') and (IV'), e.g., compounds (XIV) and (IV), respectively ("methods of the invention"), proceed on larger scale and in higher yield than prior art methods. The methods of the invention are based in part on the discovery of the importance of controlling temperature, reactant amounts and order of addition of reactants during critical steps of the methods.

DETAILED DESCRIPTION

Definitions

Figure 1:
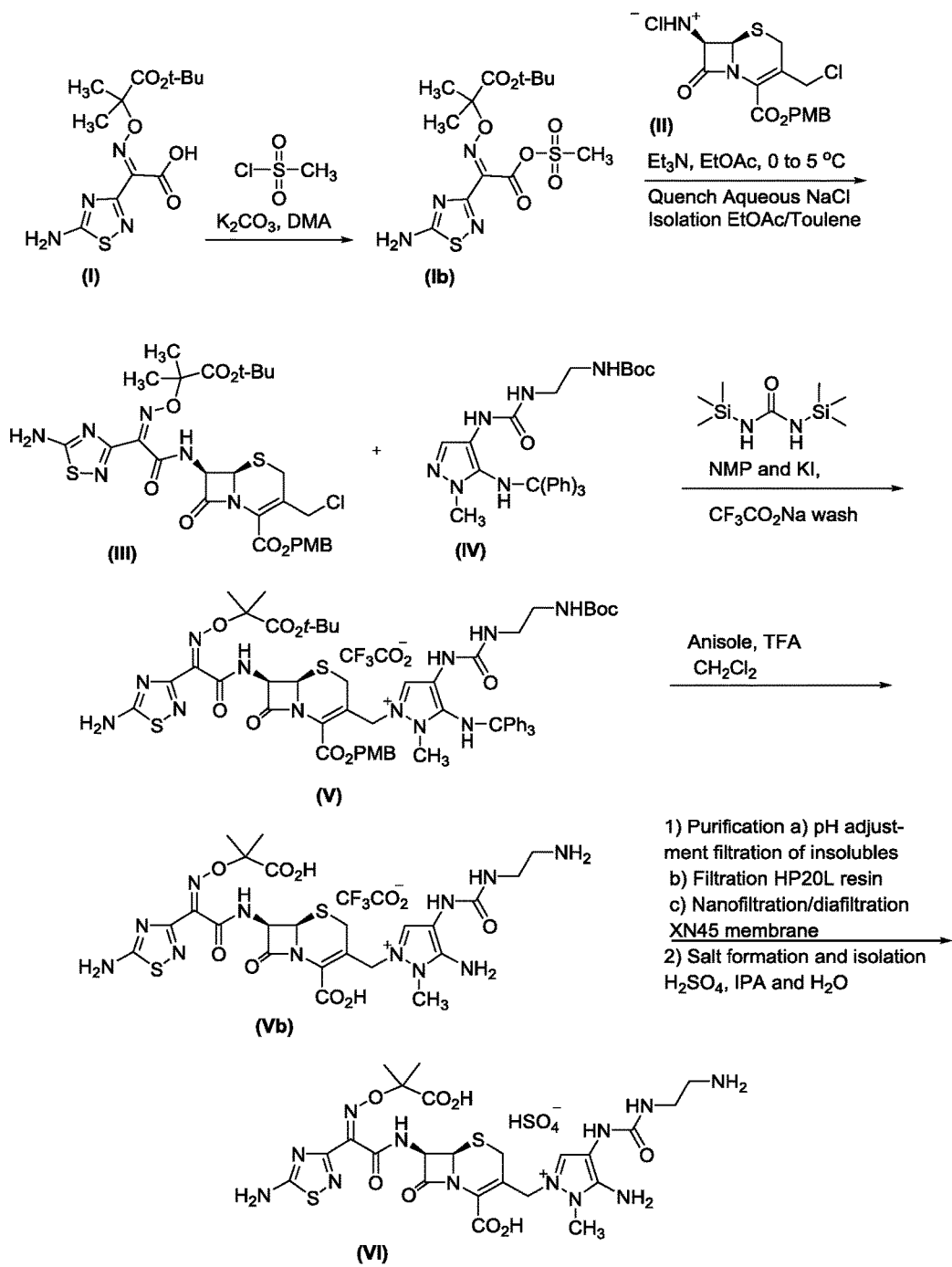
FIG. 1 shows a synthetic scheme to prepare compound (VI) (ceftolozane sulfate).
Figure 2:
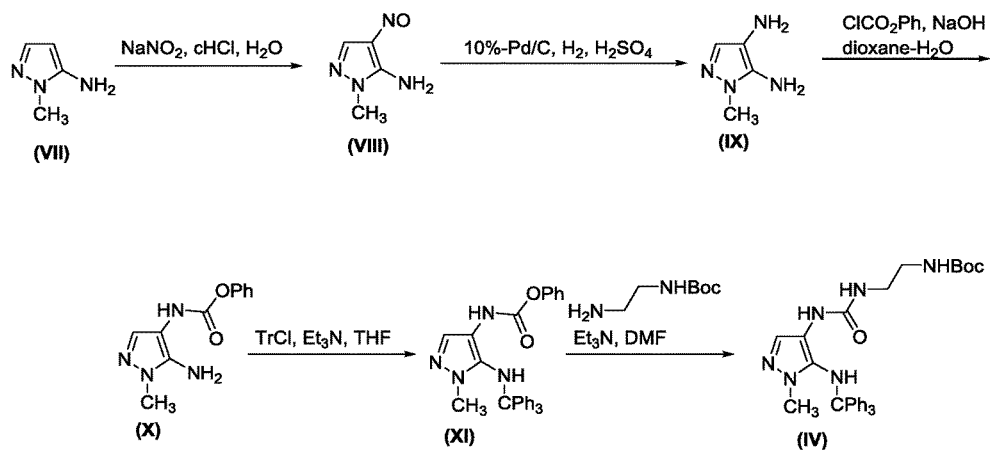
FIG. 2 shows a synthetic scheme to prepare intermediate compound (IV).
Figure 3:
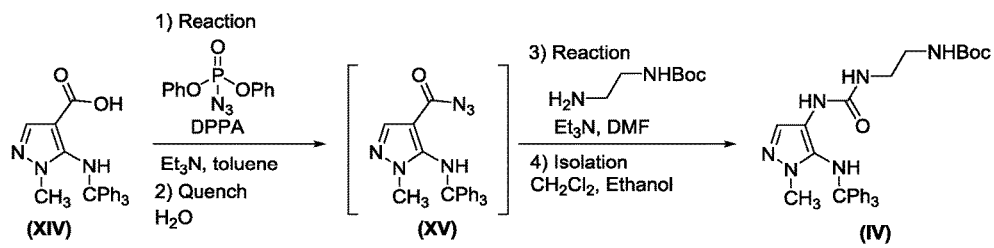
FIG. 3 shows a synthetic scheme to prepare compound (IV) from compound (XIV).
Figure 4:
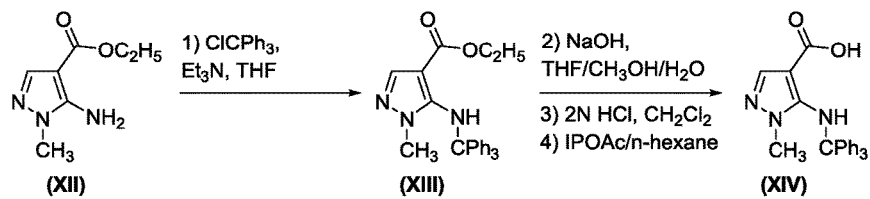
FIG. 4 shows a synthetic scheme to prepare intermediate compound (XIV) from compound (XII).

Unless otherwise defined herein, scientific and technical terms used in connection with the present disclosure shall have the meanings that are commonly understood by those of ordinary skill in the art.

The term "$C_{x\text{-}y}$ alkyl" refers to unsubstituted saturated hydrocarbon groups, including straight-chain alkyl and branched-chain alkyl groups that contain from x to y carbons in the chain. For example, $C_{2\text{-}6}$ alkyl is an alkyl group having two to six carbons. A "linear $C_{x\text{-}y}$ alkyl" refers to the "n" form of the alkyl group, for example, a "linear $C_6$ alkyl" is n-hexyl.

The term "$C_{x\text{-}y}$ alkylene" refers to unsubstituted saturated divalent hydrocarbon groups, including straight-chain alkylene and branched-chain alkylene groups that contain from x to y carbons in the chain. For example, $C_{2\text{-}6}$ alkylene is an alkylene group having two to six carbons.

The term "hydroxyalkyl" refers to an alkyl group having one or more, e.g., one, two, or three, hydroxy (i.e., —OH) substituents.

As used herein, a "protecting group" is a moiety that masks the chemical reactivity of a functional group during one or more reactions. In an illustrative example, a nitrogen protecting group such as tert-butoxycarbonyl (i.e., tert-butyloxycarbonyl, Boc, or BOC) can be introduced at one step to mask the chemical reactivity of a protected nitrogen during one reaction then removed under acidic conditions to allow the formerly protected nitrogen to undergo reaction, e.g., alkylation. A protecting group can be any one known in the art, such as those described in Wuts, P. G. M.; Greene, T. W. Greene's Protective Groups in Organic Synthesis, 4$^{th}$ ed; John Wiley & Sons: Hoboken, N.J., 2007, or any one that is developed in the future.

Oxygen and nitrogen protecting groups are known to those of skill in the art. Oxygen protecting groups include, but are not limited to, methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. Nitrogen protecting groups include, but are not limited to, carbamates (including methyl, ethyl and substituted ethyl carbamates (e.g., Troc), to name a few), amides, cyclic imide derivatives, N-alkyl and N-aryl amines, benzyl amines, substituted benzyl amines, trityl amines, imine derivatives, and enamine derivatives, for example.

In some embodiments, the oxygen protecting group is a base-labile protecting group (i.e., one that can be removed under basic conditions), such as a methyl group when used as an ester to protect a carboxylic acid. In some embodiments, the oxygen protecting group is an acid-labile oxygen protecting group (i.e., one that can be removed under acid conditions), such as tert-butyl, 4-methoxybenzyl, or triphenylmethyl. In some embodiments, the oxygen protecting group is an oxidation-reduction sensitive oxygen protecting group, such as a benzyl ether which is removed under catalytic hydrogenation conditions. In some embodiments, the oxygen protecting group is a silyl ether, such as TBDMS, TIPS, or TES, which is removed with nucleophilic fluoride.

In some embodiments, the nitrogen protecting group is a base-labile nitrogen protecting group (i.e., one that is removed under basic conditions), such as 9-fluorenylmethyl carbamate (Fmoc). In some embodiments, the nitrogen protecting group is an acid-labile nitrogen protecting group (i.e., one that is removed under acid conditions), such as triphenylmethyl, tert-butyl, tert-butoxycarbonyl, 2-trimethylsilylethoxycarbonyl (Teoc), or 4-methoxybenzyloxycarbonyl. In some embodiments, the nitrogen protecting group is an oxidation-reduction sensitive nitrogen protecting group, such as a benzyl, which can be removed under catalytic hydrogenation conditions.

As used herein, a "mild azide reagent" is any azide reagent known in the art which allows for conversion of a carboxylic acid to an acyl azide under mild conditions, e.g., at low temperatures such as under about 70 C, or at low pressures such as under about 1.2 atm, as would be recognized by one of skill in the art. Non-limiting examples of mild azide reagents include trichloroacetonitrile/triphenylphosphine/sodium azide (see Kim and Jang, Synlett 2008, 13, 2072-2074), cyanuric chloride/sodium azide (see Bandgar and Pandit, Tetrahedron Letters 2002, 43, 3413-3414), and diphenylphosphoryl azide. In a specific embodiment, the mild azide reagent is diphenylphosphoryl azide.

As used herein, an "aromatic solvent" is an organic solvent that comprises at least one phenyl ring. Aromatic solvents include solvents that comprise primarily one component, such as toluene, ethylbenzene, cumene, and benzene; solvents that may comprise a mixture of components, such as xylenes (predominantly a mixture of o-xylene and m-xylene); and mixtures of any of the foregoing. In some embodiments, the aromatic solvent comprises, consists essentially of, or consists of toluene.

The terms "amine" and "amino" are art-recognized and refer to both unsubstituted and substituted amines and salts thereof, e.g., a moiety that can be represented by the general formulae:

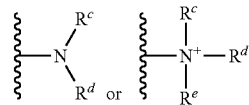

wherein $R^c$, $R^d$, and $R^e$ each independently represent a hydrogen, an alkyl, an alkenyl, —$(CH_2)_m$—$R^f$, or $R^c$ and $R^d$ taken together with the N atom to which they are attached complete a heterocycle having from 4 to 8 atoms in the ring structure; $R^f$ represents an aryl, a cycloalkyl, a cycloalkenyl, a heterocyclyl or a polycyclyl; and m is zero or an integer from 1 to 8. In preferred embodiments, only one of $R^c$ and $R^d$ is a carbonyl, e.g., $R^c$, $R^d$, and the nitrogen together do not form an imide. In even more preferred embodiments, $R^c$ and $R^d$ (and optionally $R^e$) each independently represent a hydrogen, an alkyl, an alkenyl, or —$(CH_2)_m$—$R^f$. In certain embodiments, the amino group is basic, meaning the protonated form has a $pK_a \geq 7.00$.

As used herein, an "organic base" is an organic solvent comprising at least one basic amino group. The organic base may comprise an alkyl amine, such as triethylamine, diethylamine, and/or diisopropylethylamine, and/or a cyclic amine, such as morpholine, piperidine, piperazine, pyrrolidine, cyclobutylamine, and/or cycloheptylamine.

As used herein, an alcohol solvent includes a solvent that is or comprises a hydroxyalkyl group. Exemplary alcohols include methanol, ethanol, isopropanol, n-propanol, n-butanol, sec-butanol, tert-butanol, and n-pentanol.

General Synthesis of a Compound of Formula (IV')

In one aspect, provided herein is a method of making a compound of formula (IV'), e.g., compound (IV). A general approach to make a compound of formula (IV'), e.g., compound (IV), is shown in Scheme 1 below.

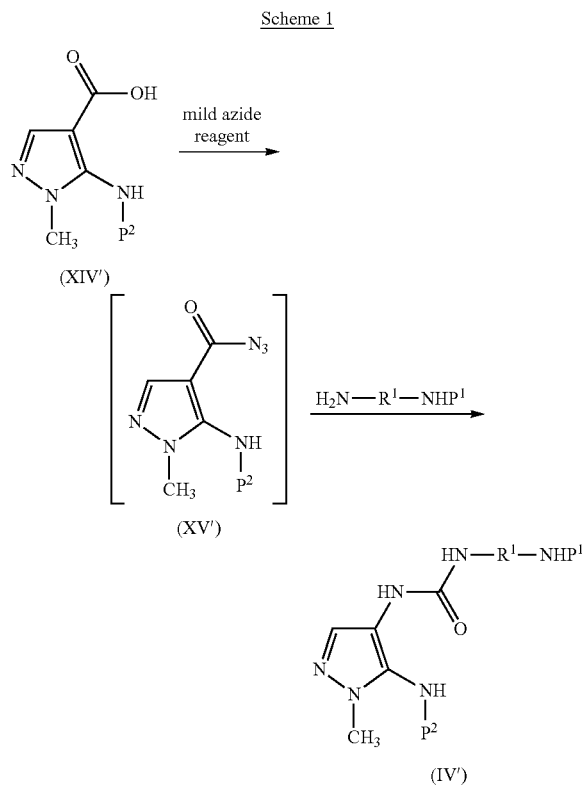

A compound of formula (XIV') is converted to a compound of formula (XV') by admixing with a mild azide reagent, such as one that allows for conversion to the acyl azide under gentle heating conditions, e.g., under 70° C. In some embodiments, the temperature is from about 20° C. to about 45° C., e.g., from about 20° C. to about 40° C., from about 25° C. to about 40° C., from about 35° C. to about 45° C., or from about 30° C. to about 40° C.

In some embodiments, the mild azide reagent is diphenylphosphoryl azide.

The reaction time for conversion of a compound of formula (XIV') to a compound of formula (XV') depends on the mild azide reagent used and reaction temperature. In some embodiments, the reaction time is from about 0.5 hours to about 24 hours, such as from about 1 hour to about 12 hours, such as from about 1 hour to about 6 hours, from about 1 hour to about 4 hours, from about 1 hour to about 3 hours, from about 2 hours to about 6 hours, from about 2 hours to about 5 hours, or from about 2 hours to about 4 hours.

In some embodiments, the admixture comprises an organic solvent. Suitable organic solvents include, but are not limited to, aromatic solvents, such as benzene, toluene, xylenes, cumene, and ethylbenzene. In certain embodiments, the admixture comprises toluene.

In some embodiments, the admixture comprises an organic base, e.g., to catalyze the reaction of the mild azide reagent with the compound of formula (XIV'). Suitable organic bases include, but are not limited to, triethylamine, diethylamine, dimethylamine, diisopropylethylamine, and N-methylmorpholine. In certain embodiments, the admixture comprises triethylamine.

In some embodiments, $P^2$ is an acid-labile nitrogen protecting group, such as triphenylmethyl or tert-butyl. In certain embodiments, $P^2$ is triphenylmethyl.

In some embodiments, the compound of formula (XV') is purified. Purification can comprise a number of methods, including chromatography (e.g., silica gel chromatography), filtration, and/or a wash (e.g., by a non-miscible solvent to remove impurities and/or side products, such as an alcohol wash or an aqueous wash). In an illustrative example, a solution comprising the compound of formula (XV') and an organic solvent is purified by one or more, e.g., 1, 2, 3, or 4 or more, aqueous washes. In one embodiment, after the aqueous wash, the organic solution is dried and concentrated, e.g., by evaporation under reduced pressure, before the subsequent step.

An amine of formula (XVI') is added to the admixture comprising the compound of formula (XV') to afford a compound of formula (IV'). The compound of formula (XVI') can be added neat directly to the admixture or as a solution comprising an organic solvent, such as an aromatic solvent, e.g., toluene. In some embodiments, the compound of formula (XVI') is added slowly over a period of time, such as from about 0.5 hour to about 12 hours, such as from about 1 hour to about 6 hours, from about 1 hour to about 4 hours, from about 1 hour to about 3 hours, from about 1 hour to about 2 hours, from about 2 hours to about 5 hours, from about 2 hours to about 4 hours, or from about 2 hours to about 3 hours.

In some embodiments, $R^1$ is $C_{2-6}$ alkylene, e.g., ethylene, such as an ethylene group that is 1, 2-disubstituted.

In some embodiments, $P^1$ is an acid-labile nitrogen protecting group, such as tert-butoxycarbonyl, 2-trimethylsilylethoxycarbonyl, or 4-methoxybenzyloxycarbonyl. In certain embodiments, $P^1$ is tert-butoxycarbonyl.

After adding the compound of formula (XVI') to the admixture comprising the compound of formula (XV'), the reaction is heated to a temperature of from about 70° C. to about 110° C., such as from about 80° C. to about 100° C., from about 75° C. to about 95° C., from about 80° C. to about 110° C., from about 85° C. to about 105° C., or from about 70° C. to about 100° C.

After completion of the addition of the compound of formula (XVI'), the resultant admixture is further aged for an amount of time to complete the formation of the compound of formula (IV'). In some embodiments, the additional reaction time is from about 0.5 hour to about 12 hours, such as from about 1 hour to about 6 hours, from about 1 hour to about 5 hours, from about 1 hour to about 4 hours, from about 1 hour to about 3 hours, from about 1 hour to about 2 hours, from about 2 hours to about 5 hours, from about 2 hours to about 4 hours, or from about 2 hours to about 3 hours.

In some embodiments, a compound of formula (XIV') has the structure of compound (XIV) as described herein.

In some embodiments, a compound of formula (XV') has the structure of compound (XV) as described herein.

In some embodiments, a compound of formula (IV') has the structure of compound (IV) as described herein.

Compound (IV) is also known as "UBT" and "tert-butyl (2-(3-(1-methyl-5-(tritylamino)-1H-pyrazol-4-yl)ureido)ethyl)carbamate". Compound (XIV) is also known as "PCA" and "1-methyl-5-(tritylamino)-1H-pyrazole-4-carboxylic acid". Compounds (IV) and (XIV) have the structures shown below.

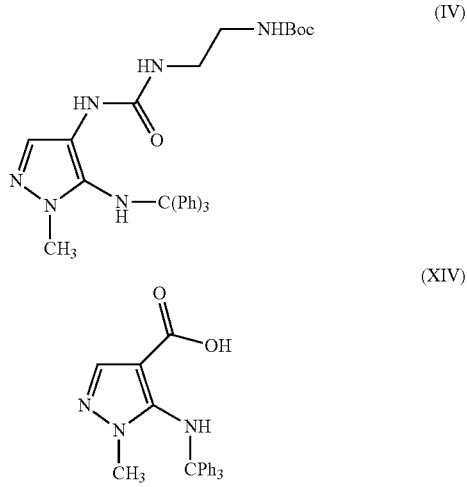

Also provided is the preparation of compound (VI) from a compound of formula (IV'), e.g., compound (IV), prepared by any one of the methods as described herein. In an illustrative example, compound (IV) prepared by Method 2 described below is suitable for use in any synthetic scheme known in the art, e.g., the synthetic route shown in FIG. 1, for the preparation of compound (VI) (ceftolozane sulfate).

In another aspect, provided herein is a method of making compound (IV) comprising the steps of: (a) forming a mixture comprising diphenylphosphoryl azide and compound (XIV); (b) adding a solvent comprising water; (c) adding NBOC-EDA; (d) filtering the mixture and collecting a wet cake comprising crude product; and (e) obtaining compound (IV).

In one embodiment, step (a) comprises: (1) forming a mixture comprising toluene, triethylamine, 1.2 equivalents of diphenylphosphoryl azide, and 1.0 equivalent of compound (XIV) while maintaining the temperature of the mixture below 40° C.; (2) adjusting the temperature of the mixture to 45° C. and agitating for at least about 1 hour; (3) adjusting the temperature of the mixture to below 40° C.; (4) adding 0.2 equivalents of diphenylphosphoryl azide while maintaining the temperature of the mixture below 40° C.; and (5) adjusting the temperature of the mixture to 45° C. and agitating the mixture for at least 1 hour.

In one embodiment, step (b) comprises: (1) adjusting the temperature of the mixture to 25° C.; (2) adding the solvent comprising water while maintaining the temperature of the mixture at about 25° C.; (3) agitating the mixture at 25° C. for at least 10 minutes; and (4) discarding the lower aqueous phase after phase separation.

In another embodiment, (b) comprises: (1) adding the solvent comprising water while maintaining the temperature of the mixture at about 25° C.; (2) agitating the mixture at 25° C. for at least 10 minutes; (3) discarding the lower aqueous phase after phase separation; and (4) drying the organic phase by distillation at a temperature less than 40° C.

In one embodiment, step (c) comprises adding NBOC-EDA in two portions. In another embodiment, step (c) comprises: (1) adding 5.7 volumes of toluene; (2) adding 0.19 equivalents of NBOC-EDA; (3) adjusting the temperature to 90° C.; (4) adding a further 0.81 equivalents of NBOC-EDA in toluene while maintaining the temperature of the mixture at 90° C.; and (5) agitating the mixture at 90° C. for 4 to 5 hours.

In one embodiment, step (d) comprises: (1) adjusting the temperature of the mixture to 30° C.; (2) agitating the mixture at 30° C. for at least one hour; and (3) filtering the mixture to collect the wet cake comprising crude product.

In one embodiment, step (d) further comprises washing the wet cake with 2.3 volumes of toluene. The wet cake comprising crude product can also be washed with a mixture of dichloromethane and ethanol.

In one embodiment, step (e) comprises: (1) concentrating the organic phase to 6 to 8 volumes; (2) adjusting the temperature to 3° C.; (3) agitating the mixture at 3° C. for at least one hour; and (4) filtering the reaction mixture to collect a wet cake. In another embodiment, step (e) further comprises: (4) washing the wet cake with 1.3 volumes of cold ethanol; and (5) drying the product under reduced pressure with a nitrogen purge.

In another aspect, provided herein is a method of making compound (XIV) comprising the steps of: (a) forming a mixture comprising triethylamine and compound (XII); (b) adding trityl chloride (ClCPh$_3$) to the mixture of step (a); (c) adding an aqueous solution comprising sodium hydroxide; (d) adding an aqueous solution comprising hydrochloric acid; (e) adding isopropyl acetate and n-heptane; and (f) obtaining compound (XIV).

In one embodiment, step (a) comprises combining 1.5 equivalents of triethylamine, 1.0 equivalent of compound (XII) and 5.0 volumes of tetrahydrofuran to yield the mixture.

In one embodiment, step (b) comprises: (1) adding 1.2 equivalents of trityl chloride while maintaining the temperature of the mixture between 20 and 40° C.; and (2) adjusting the temperature of the mixture to 65° C.; and (3) agitating the mixture at 65° C. for 11 to 16 hours.

In one embodiment, step (c) comprises: (1) adjusting the temperature of the mixture to between 25 and 35° C.; (2) adding the aqueous solution comprising 2.5 equivalents of sodium hydroxide, 0.7 equivalents of water and 4.0 volumes of methanol while maintaining the temperature of the mixture between 25 and 50° C.; (3) adjusting the temperature to 65° C.; and (4) agitating the mixture at 65° C. for 11 to 16 hours.

In one embodiment, (d) comprises: (1) adjusting the temperature of the mixture to between 0 and 10° C.; (2) adding the aqueous solution comprising 3.4 volumes of 2N hydrochloric acid to adjust the pH to between 9 and 10 while maintaining the temperature of the mixture between 0 and 10° C.; (3) adding 6.0 volumes of dichloromethane while maintaining the temperature of the mixture between 0 and 10° C.; (4) adding the aqueous solution comprising 3.2 volumes of 2N hydrochloric acid to adjust the pH to between 6.5 and 7.5 while maintaining the temperature of the mixture between 0 and 10° C.; and (5) discarding the aqueous layer after phase separation.

In one embodiment, step (e) comprises: (1) concentrating the organic layer to 8 to 9 volumes; (2) adding 5.0 volumes of isopropyl acetate; (3) concentrating the mixture to 8 to 9 volumes while maintaining the temperature below 40° C.; (4) adjusting the temperature of the mixture to between 30 and 40° C.; and (5) adding 9.8 volumes of isopropyl acetate.

In one embodiment, step (f) comprises: (1) concentrating the mixture to 10 to 12 volumes while maintaining the temperature below 40° C.; (2) adjusting the temperature to between −10 and 0° C.; (3) agitating the mixture at between −10 and 0° C. for 2 to 3 hours; and (4) filtering the reaction mixture to collect a wet cake. In another embodiment, step (f) further comprises: (5) washing the wet cake with a mixture of 2:1 (v/v) n-heptane:isopropyl acetate 1.3 volumes; and (6) drying the product under reduced pressure with heat.

Method of Making Compound (XIV) (Method 1)

Method 1 is represented by the following scheme:

Scheme 2

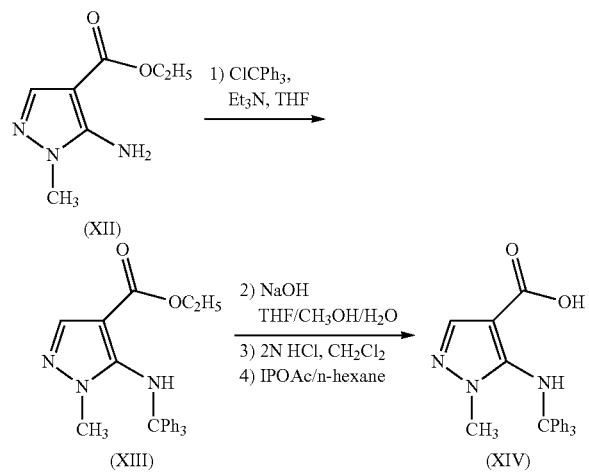

TABLE 1

Materials for the preparation of compound (XIV)

| Material | MW (g/mol) | Weight (g) | mMoles | Molar Equivalents | Mass (w/w) | Density |
|---|---|---|---|---|---|---|
| Compound (XII) | 169.18 | 50.0 | 296 | 1.0 | 1.0 | |
| TrCl | 278.78 | 99.0 | 355 | 1.2 | 2.0 | |
| Et$_3$N | 101.19 | 44.9 | 443 | 1.5 | 0.9 | 0.73 |
| 30% NaOH | 39.66 | 110.0 | 739 | 2.5 | 2.2 | |
| 2N HCl | | 400.0 | | | 8.0 | |
| THF | | 225.0 | | | 4.5 | 0.89 |
| MeOH | | 160.0 | | | 3.2 | 0.79 |
| H$_2$O | | 36.0 | | | 0.7 | 1.00 |
| CH$_2$Cl$_2$ (DCM) | | 400.0 | | | 8.0 | 1.33 |
| IPOAc | | 710.0 | | | 14.2 | 0.87 |
| n-heptane | | 90.7 | | | 1.8 | 0.68 |
| Compound (XIV) (theoretical) | 383.44 | 113.0 | | | | |
| Compound (XIV) (isolated) | 383.44 | 90.7 | | | | |
| Isolated yield | | 80.0% | | | | |

TABLE 2

List of in-process controls for Method 1

| Analytical Test | Analytical Method | Acceptance Criteria |
|---|---|---|
| Conversion of compound (XII) to compound (XIII) | HPLC | ≤1.0% |
| Conversion of compound (XIII) to compound (XIV) | HPLC | ≤1.0% |

TABLE 2-continued

List of in-process controls for Method 1

| Analytical Test | Analytical Method | Acceptance Criteria |
|---|---|---|
| pH before adding CH$_2$Cl$_2$ | pH paper | 9-10 |
| pH after adding CH$_2$Cl$_2$ | pH meter | 6.5-7.5 |
| Residual compound (XIII) in supernatant | HPLC | ≤20 mg/mL |
| Water content in dry compound (XIV) | KF | ≤2% |
| Assay of compound (XIV) | HPLC | ≥86.0% |

Method of Making Compound (IV) (Method 2)

Method 2 is represented by the following scheme:

Scheme 3

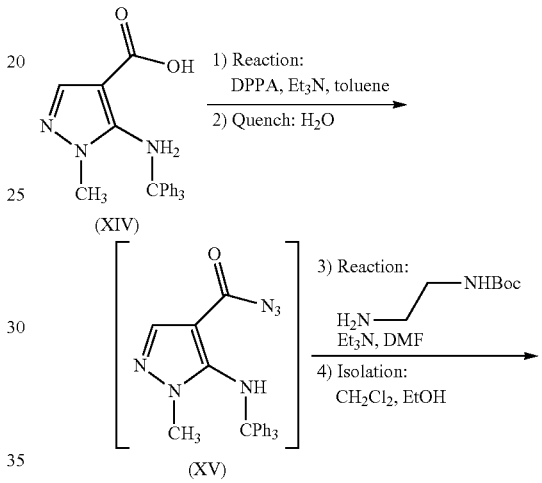

TABLE 3

Materials for the preparation of compound (IV)

| Material | MW (g/mol) | Weight (g) | mMoles | Molar Equivalents | Mass (w/w) | Density |
|---|---|---|---|---|---|---|
| Compound (XIV) | 383.44 | 100.0 | 260.80 | 1.0 | 1.00 | |
| NBOC-EDA | 160.21 | 41.8 | 260.80 | 1.0 | 0.42 | |
| Diphenylphosphoryl Azide (DPPA) | 275.20 | 100.4 | 365.12 | 1.4 | 1.0 | |
| Et$_3$N | 101.19 | 52.8 | 521.59 | 2.0 | 0.53 | 0.73 |
| Toluene | | 1600.0 | | | 16.0 | 0.87 |
| Ethanol (EtOH) | | 900.0 | | | 9.0 | 0.87 |
| CH$_2$Cl$_2$ (DCM) | | 600.0 | | | 6.0 | 1.33 |
| Compound (IV) (theoretical) | 540.66 | 141.0 | | | | |
| Compound (IV) (isolated) | 540.66 | 109 | | | | |
| Isolated yield | | 77.3% | | | | |

A comparison of alternate processes used to synthesize compound (IV) and related intermediates is summarized in Table 4.

TABLE 4

Alternative processes for synthesis of compound (IV)

| Comparative method | Method 2 | Advantages of Method 2 |
|---|---|---|
| The reaction to form compound (XV) was carried out at 35° C. | The reaction to form compound (XV) is carried out at 45° C. | Improved cycle time |
| NBOC-EDA was added in a single portion once batch reached the reaction temperature. | NBOC-EDA is added in two portions, with the first portion added before adjusting the batch to the reaction temperature. | Improved yield: 45% yield in comparative method versus 85% yield in Method 2 |
| An aqueous wash was carried out after the preparation of compound (IV). Distillation of compound (XV) at up to 50° C. | An aqueous wash is carried out after the preparation of compound (XV). Distillation of compound (XV) at no more than 40° C. | Improved yield: 45% yield in comparative method versus 85% yield in Method 2 Distillation of compound (XV) at more than 40° C. results in decomposition and the formation of impurities. |

Table 4 indicates certain advantageous aspects of the improved Method 2 directed to a method of making a compound of formula (IV'), e.g., compound (IV), as compared with the initial comparative method. First, the reaction temperature used to form a compound of formula (XV'), e.g., compound (XV), is increased from about 35° C. to about 45° C. As further described in Table 5 below, the reaction temperature is non-critical, and its increase allows for a corresponding decrease in required reaction time, and thus an improved cycle time. Second, after formation of a compound of formula (XV'), e.g., compound (XV), the addition of a compound of formula (XVI'), e.g., NBOC-EDA, to the admixture comprising a compound of formula (XV') is performed portionwise over a period of time, rather than in a single portion. Third, an aqueous wash of the admixture comprising a compound of formula (XV'), e.g., compound (XV), purifies the compound of formula (XV') prior to the addition of a compound of formula (XVI'). The purification comprising an aqueous wash does not appreciably degrade a compound of formula (XV'). In this illustrative example, the aqueous wash provides for an increased yield of compound (IV) (about 85% yield as compared to about 45% yield in the initial method).

Table 5 summarizes the parameters which were evaluated for the reaction to prepare compound (XV) and its quench along with proven acceptable ranges (PARs) and criticality assessments including impact on the critical quality attributes (CQAs). Here, "non-critical" is defined as an easily controlled process parameter with no impact on quality and/or yield or acceptable process performance within a wide range of acceptable values, and "key" is defined as having a minor impact on quality and/or yield that should be maintained within a specified range to ensure process performance, consistency and robustness. DPPA was a key process parameter, below the normal operating range (NOR), the yield of compound (IV) was reduced.

TABLE 5

Parameters for the reaction to prepare compound (XV)

| Parameter | PAR/NOR | Criticality Assessment | Justification of Criticality Assessment |
|---|---|---|---|
| Et$_3$N (equiv) | 1.5 to 3.0 1.9 to 2.1 | Non-Critical | No risk to drug substance CQAs, wide PAR, low deviation risk. |
| DPPA (equiv) | 1.1 to 2.0 1.2 to 1.8 | Key | Above PAR: wasteful. Below PAR: reduced yield. No impact on product purity. |
| Toluene (vol) | ≥8.0 9.0 to 9.4 | Non-Critical | No risk to drug substance CQAs, wide PAR, low deviation risk. |
| Reaction temperature (° C.) | 30 to 55 40 to 50 | Non-Critical | No risk to drug substance CQAs, wide PAR, low deviation risk. |
| Batch temperature after cooling (° C.) | 15 to 45 20 to 30 | Non-Critical | No risk to drug substance CQAs, wide PAR, low deviation risk. |
| Total water wash (vol) | ≥3.0 7.6 to 8.4 | Non-Critical | No risk to drug substance CQAs, wide PAR, low deviation risk. |
| Batch temperature during distillation (° C.) | 20 to 40 20 to 40 | Key | >40 leads to decomposition and formation of impurities |

Table 6 summarizes the parameters which were evaluated for the reaction to prepare compound (IV) along with proven acceptable ranges (PARs) and criticality assessments including impact on the critical quality attributes (CQAs). Here, "non-critical" is defined as an easily controlled process parameter with no impact on quality and/or yield or acceptable process performance within a wide range of acceptable values, and "key" is defined as having a minor impact on quality and/or yield that should be maintained within a specified range to ensure process performance, consistency and robustness. There are three key process parameters, operation outside of the normal operating range will reduce the yield of compound (IV).

TABLE 6

Parameters for the reaction to prepare compound (IV)

| Parameter | PAR/NOR | Criticality Assessment | Justification of Criticality Assessment |
|---|---|---|---|
| Toluene (vol) | ≥4.0 5.6 to 5.9 | Non-Critical | No risk to drug substance CQAs, wide PAR, low deviation risk. |
| First portion of NBOC-EDA (equiv) | 0.15 to 0.30 0.17 to 0.21 | Key | Below PAR: reduced yield. Above PAR: reduced yield. No impact on product purity. |
| Second portion of NBOC-EDA (equiv) | 0.75 to 1.5 0.78 to 0.83 | Key | Below PAR: reduced yield. No impact on product purity. |
| Reaction temperature (° C.) | 80 to 100 85 to 95 | Key | Below PAR: reduced yield. Above PAR: reduced yield. No impact on product purity. |

Table 7 summarizes the parameters which were evaluated for the isolation of compound (IV) along with proven acceptable ranges (PARs) and criticality assessments including impact on the critical quality attributes (CQAs). Here, "non-critical" is defined as an easily controlled process parameter with no impact on quality and/or yield or acceptable process performance within a wide range of acceptable values, and "key" is defined as having a minor impact on quality and/or yield that should be maintained within a specified range to ensure process performance, consistency and robustness. All process parameters were non-critical.

TABLE 7

Parameters for isolation of compound (IV)

| Parameter | PAR/NOR |
|---|---|
| Initial cooling temperature (° C.) | 15 to 90/20 to 40 |
| Toluene for wash (vol) | ≥2.0/4.4 to 4.8 |
| Dichloromethane for slurry (vol) | ≥3.0/4.4 to 4.6 |
| Total ethanol for wash and slurry (vol) | ≥5.0/10.3 to 12.3 |
| Batch volume after concentration (vol) | 4 to 8/6 to 8 |
| Product isolation temperature (° C.) | −10 to 25/−5 to 10 |

TABLE 8

List of in-process controls for Method 2

| Analytical Test | Analytical Method | Target Results |
|---|---|---|
| Conversion of compound (XIV) to compound (XV) | HPLC | ≤1.0% |
| Water content in compound (XV) solution after distillation | KF | ≤0.05% |
| Conversion of compound (XV) to compound (IV) | HPLC | ≤2.0% |
| Water content in compound (IV) during drying | KF | ≤0.2% |
| Residual solvents in compound (IV) during drying | | |
| Toluene | GC | ≤5000 ppm |
| CH$_2$Cl$_2$ | | ≤5000 ppm |
| EtOH | | ≤5000 ppm |
| Et$_3$N | | ≤320 ppm |
| Assay of compound (IV) | HPLC | ≥98% |

Synthetic Compositions

Compound (IV) is a useful intermediate in the production of cephalosporin antibiotics, particularly ceftolozane, and salts thereof. Compositions comprising compound (IV) and intermediates are provided herein. Also provided are compositions produced or occurring during the methods of making compound (IV).

The following compositions may be produced during the methods of the invention to prepare compound (XIV) using Method 1: a composition comprising compounds (XII) and (XIII); a composition comprising compounds (XIII) and (XIV); a composition comprising compounds (XII), (XIII) and (XIV); and a composition comprising compound (XIII) and a slat of compound (XIV), e.g., a sodium salt.

The following compositions may be produced during the methods of the invention to prepare compound (IV) using Method 2: a composition comprising compounds (XIV) and (XV); a composition comprising compounds (XV) and (IV); and a composition comprising compounds (XIV), (XV) and (IV). Compositions produced during Method 2 may further comprise one or more impurities of Tables 10 or 11. In some embodiments, compositions produced during Method 2 may include characteristic byproducts of the reaction mixture. For example, characteristic byproducts of the reaction mixture may include, but are not limited to, (PhO)$_2$P(=O)OH (diphenylphosphate) or a salt thereof from DPPA or azide.

EXAMPLES

Example 1

Preparation of Compound (XIV) (1-methyl-5-(tritylamino)-1H-pyrazole-4-carboxylic acid)

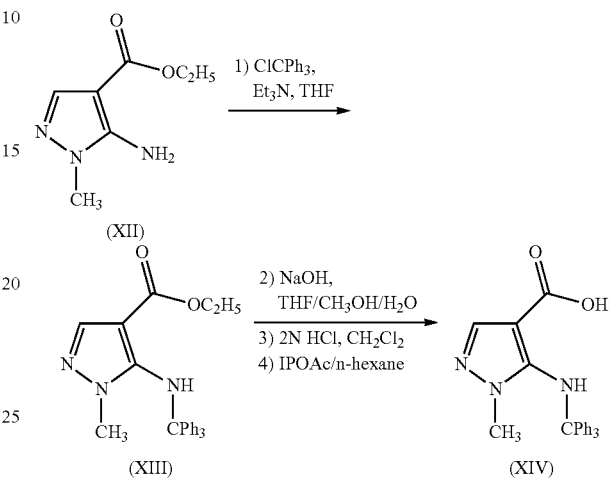

Preparation of Compound (XIII)

Tetrahydrofuran (THF, 225.0 g, 253 mL, 5.0 vol), compound (XII) (ethyl 5-amino-1-methyl-1H-pyrazole-4-carboxylate, 50.0 g, 1.0 equiv, active amount), and triethylamine (Et$_3$N, 44.9 g, 1.5 equiv) were added to the batch. Trityl chloride (TrCl, ClCPh$_3$, 99.0 g, 1.2 equiv) was added to the batch at a temperature between 20 and 40° C. The temperature was adjusted to 65° C., and the batch was agitated for 11 to 16 hours, or until completion of the reaction (≤1.0% of compound (XII) remaining).

The solvents, reagents, stoichiometry, temperatures and reaction times of step (1) were selected in order to maximize the formation of compound (XIII).

Preparation of Compound (XIV)

The batch temperature was adjusted to 25 to 35° C. Water (36.0 g, 36.0 mL, 0.7 eq), 30% aq. NaOH (110.0 g, 2.5 eq) and CH$_3$OH (160.0 g, 200.0 mL, 4.0 vol) were added to the reactor at 25 to 50° C. The temperature was adjusted to 65° C., and the batch was agitated for 11 to 16 hours, or until completion of the reaction. The batch was adjusted to 0 to 10° C. 2N HCl (169.0 g, 3.4 vol) was added to the reactor and the pH was adjusted to 9 to 10 at 0 to 10° C. Dichloromethane (DCM, CH$_2$Cl$_2$, 400.0 g, 6.0 vol) was added to the batch at 0 to 10° C. 2N HCl (162.2 g, 3.2 vol) was added to the batch and the pH as adjusted to 6.5 to 7.5 at 0-10° C. The agitation was stopped, and the phases were allowed to separate for 0.5 to 1 hour. The aqueous layer was discarded. The solvents, reagents, stoichiometry, temperatures and reaction times of step (2) were selected in order to maximize the formation of compound (XIV).

Isolation of Compound (XIV)

The organic layer was concentrated to 8 to 9 volumes by distillation at <40° C. under reduced pressure. Isopropyl acetate (IPOAc, 218.0 g, 5.0 vol) was added to the batch. The batch was concentrated to 8 to 9 volumes by distillation at <40° C. under reduced pressure. The temperature was adjusted to 30 to 40° C. IPOAc (400.0 g, 9.8 vol) was added to the batch at 30 to 40° C. The batch was concentrated to 10 to 12 volumes by distillation at <40° C. under reduced pressure. The temperature was adjusted to −10 to 0° C. for 4 to 8 hours. The batch was stirred for 2 to 3 hours at −10 to 0° C. The batch was filtered. The cake was washed with 148.7 g of n-heptane:IPOAc(v/v)=2:1 (90.7 g n-heptane and 58.0 g IPOAc). The solid was dried under vacuum at 40 to 45° C. for 6 to 7 hours. The solid was dried under reduced pressure at 70 to 75° C. for 40 to 120 hours. The solvents, stoichiometry, temperatures and reaction times of step (3) were selected in order to maximize the isolated yield of compound (XIV).

Example 2

Preparation of Compound (IV) (tert-butyl (2-(3-(1-methyl-5-(tritylamino)-1H-pyraol-4-yl)ureido)-ethyl) carbamate Preparation of Compound (XV)

The reactor was charged with toluene (800 g, 920 mL, 9.2 vol), compound (XIV) (100 g, 1.0 equiv, active amount), triethylamine (Et$_3$N, 52.78 g, 2.0 equiv), and diphenylphosphoryl azide (DPPA, 86.1 g, 1.20 equiv), while maintaining the batch temperature below 40° C. Then temperature was adjusted to 45° C., and the batch was agitated for at least 1 hour. Then the temperature was adjusted to below 40° C., and the batch was charged with DPPA (14.4 g, 0.20 equiv). The batch was adjusted to a temperature of 45° C. and agitated for at least 1 hour. The typical reaction time was between 3 and 5 hours, or until completion of the reaction.

After the reaction was deemed complete, the temperature of the batch was adjusted to 25° C., then the batch was charged with water (400 g, 4.0 vol), and was stirred for at least 10 minutes. Then the agitation was stopped, and the phases were allowed to separate for at least 15 minutes. The lower aqueous phase was discarded and the water wash was repeated. The batch was dried by distillation under reduced pressure at a temperature of no more than 40° C. Distillation at a temperature exceeding 40° C. resulted in decomposition and the formation of impurities.

Preparation of Compound (IV)

The batch from step 1 of this Example was charged with toluene (500.0 g, 5.7 vol), and the first portion of (2-aminoethyl)-carbamic acid tert-butyl ester (NBOC-EDA) (8.0 g, 0.19 equiv), via portionwise addition. The batch temperature was adjusted to 90° C. A second portion of NBOC-EDA (33.8 g, 0.81 equiv) was charged as a solution in toluene (100 g, 1.2 vol) over the course of at least 2 hours, while maintaining the batch temperature at 90° C. Typical reaction time was between 4 and 5 hours.

The batch was cooled to 30° C. over the course of at least 2 hours, and then agitated at this temperature for at least 1 hour. The batch was filtered to afford the product as a wet cake, and the wet cake was washed with toluene (200 g, 2.3 vol). The wet cake was suspended in DCM (600 g, 4.5 vol) and EtOH (600 g, 7.5 vol). Then the temperature was adjusted to 30° C., and the suspension was agitated for at least 0.5 hours. The batch was concentrated to 6 to 8 volumes by distillation under reduced pressure at a temperature less than 40° C. Subsequently, the batch was charged with EtOH (200 g, 2.5 vol) and reconcentrated to 6 to 8 volumes by distillation under reduced pressure at a temperature less than 40° C. Then the batch was cooled to 3° C. over the course of at least 1 hour, and then stirred for at least 1 hour at this temperature. The batch was filtered to afford a wet cake, which was washed with cold EtOH (100 g, 1.3 vol). The product was dried under a reduced pressure with nitrogen purge; the drier jacket was set to a temperature between 45 to 55° C. In the laboratory, the typical drying time was 12 hours whereas on commercial scale, the drying time was between 40 and 50 hours. Yield: 109 g (77% molar yield) with 99.85% HPLC purity.

Example 3

HPLC Characterization for Method 2

HPLC Conditions
The HPLC conditions are listed in Table 9 below.

TABLE 9

HPLC conditions for analysis of pyrazolyl carboxylic acid and pyrazolyl urea derivatives

| Column | Develosil ODS-UG-5, 5 µm, 250 mm × 4.6 mm, or equivalent |
|---|---|
| Guard column | Develosil ODS-UG-5, 5 µm, 10 mm × 4.0 mm, or equivalent |
| Column temperature | 45° C. ± 2° C. |
| Mode | Gradient |
| Mobile phase A | 50 mM Sodium perchlorate monohydrate, pH 2.50 |
| Mobile phase B | 63 mM Sodium perchlorate monohydrate, pH 2.50: CH$_3$CN 80:20 |

| Gradient | Time (min) | % A | % B |
|---|---|---|---|
| | 0.0 | 97.5 | 2.5 |
| | 3.0 | 73.0[a] | 27.0[a] |
| | 33.0 | 68.0[a] | 32.0[a] |
| | 63.0 | 0.0 | 100 |
| | 88.0 | 0.0 | 100 |
| | 88.1 | 97.5 | 2.5 |
| | 105.0 | 97.5 | 2.5 |

| Flow rate | 1.0 mL/minute |
|---|---|
| Detection | UV at 254 nm (ceftolozane and ceftolozane related degradants) |
| Auto-sampler temperature | 4° C. ± 2° C. |
| Injection volume | 10 µL |
| Run time | 105 minutes |

[a]The ratio of mobile phase A to mobile phase B may be adjusted to achieve the desired retention time.
The change from 3.0 to 33.0 minutes must be an increase of 5.0% mobile phase B. For example, if the mobile phase B % is set at 27.5% at 3.0 minutes, the mobile phase B % must be set at 32.5% at 33.0 min.

Sample Preparation

Samples should be prepared after the Blank and the System Suitability of the sequence are complete. The samples were equilibrated to room temperature before dilution with the diluent described above.

System Suitability

At the beginning of each run, the diluent blank and SST are each injected in singlet. The system suitability is determined using the SST. The tailing factor for the ceftolozane peak should be between 0.8 and 1.5, and the retention time for the ceftolozane peak should be 24.0 minutes±1.0 minutes. The binary pump setting between 3.0 and 33.0 minutes may be adjusted to achieve the ceftolozane peak retention time. Each sample is prepared in singlet and injected twice:

Integration and Calculations

Only impurities >LOD (0.008% Area) are integrated. The peak area percentage for each impurity >LOD is taken directly from the chromatogram. Limits:

| LOD (Area %)* | LOQ (Area %)* |
|---|---|
| 0.008% | 0.027% |

*Based on an actual area % from the chromatogram

The mean % area of each peak is calculated and the absolute difference of any peak in the two replicates cannot be >0.030%. The purity and related substances are determined based on relative area % of each peak with respect to the total peak area of the sample. The total impurities are the sum of the individual impurities >LOD. The calculations are as follows:

$$\% \text{ Impurity}(\% \text{ Area}) = \frac{Area_{impurity}}{Area_{Total}} \times 100\%$$

Where:
$Area_{impurity}$=Area of the Individual Impurity Peak
$Area_{Total}$=Total Area of all peaks >LOD including Ceftolozane $$\text{Purity}(\% \text{ Area}) = \frac{Area_{Ceftolozane}}{Area_{Total}} \times 100\%$$

Where:
$Area_{Ceftolozane}$=Area of the Ceftolozane Peak
$Area_{Total}$=Total Area of all peaks >LOD including Ceftolozane Total Impurities (% Area)=100−Purity (% Area)

Compound (XIV) is the starting material in Method 2 for the synthesis of compound (IV) (Table 10; entry 1). Based on purging studies, the maximum estimated level for compound (XIV) was calculated to be less than $1.08 \times 10^{-5}$ ppm in the drug substance; therefore, an in silico assessment of mutagenic potential was deemed unnecessary, in accordance with ICH M7, *Assessment and Control of DNA Reactive (Mutagenic) Impurities in Pharmaceuticals to Limit Potential Carcinogenic Risk*, February 2013.

The measured level of compound (XV) (Table 10; entry 2), a non-isolated intermediate, in the synthesis of compound (IV) was less than 16 ppm in the 23 batches tested. This demonstrates that compound (XV) is well controlled in the manufacturing process.

TABLE 10

List of starting materials and structurally related impurities in Method 2

| Entry | Substance/Origin | Fate | Cumulative Purging Factor | Maximum Estimated and Measured Levels in Drug Substance Batches |
|---|---|---|---|---|
| 1 | Compound (XIV) 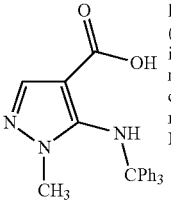 $C_{24}H_{21}N_3O_2$ MW = 383.4 Regulatory starting material | Consumed in Method 2 to form compound (XV) (IPC 1.0% or less); any unreacted compound (XIV) is removed during isolation of compound (IV); measured: <16 ppm in compound (IV); n = 5; LOQ = 16 ppm | $3.27 \times 10^9$ | Estimated: $1.08 \times 10^{-5}$ ppm Measured: <LOQ n = 4 (LOQ = 0.23 ppm) |
| 2 | Compound (XV) 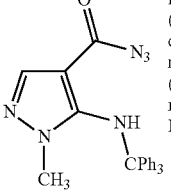 $C_{24}H_{20}N_6O$ MW = 408.5 Non-isolated intermediate | Consumed in Method 2 to form compound (IV) (IPC 2.0% or less); unreacted compound (XV) removed during isolation of compound (IV); measured: ≤16 ppm in compound (IV); n = 23; LOQ = 1.5 ppm | $8.12 \times 10^{-5}$ ppm | Measured: <LOQ n = 6 (LOQ = 3 ppm) |

TABLE 10-continued

List of starting materials and structurally related impurities in Method 2

| Entry | Substance/Origin | Fate | Cumulative Purging Factor | Maximum Estimated and Measured Levels in Drug Substance Batches |
|---|---|---|---|---|
| 3 | Triphenylmethanol 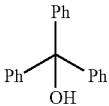 C$_{19}$H$_{16}$O<br>MW = 260.3<br>Cas Number:<br>76-84-6<br>Impurity in Method 2 | Removed in Method 2 measured: ≤0.2% in compound (IV)<br>n = 20 (LOQ = 0.05%) | >60 | Measured: <LOQ<br>n = 6<br>(LOQ = 20 ppm) |

The reagents and their by-products formed in Method 2 are listed in Table 11. The reagents used in the process are all considered standard reagents used in the production of pharmaceuticals and are readily available in bulk quantities from a number of suppliers. Multiple manufacturing batches of compound (IV) have been tested for residual diphenylphosphoryl azide (DPPA), triethylamine, diphenyl phosphate and azide (Table 11; entries 1, 3, 4 and 5); all were controlled to ppm levels. Notably, the level of diphenylphoshoryl azide was found to be ≤2.4 ppm and azide <5 ppm in 29 batches of compound (IV).

TABLE 11

List of starting materials and structurally related impurities in Method 2

| Entry | Substance | Control/Fate | Measured Levels in Drug Substance |
|---|---|---|---|
| 1 | Diphenylphosphoryl azide (DPPA) 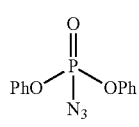 C$_{12}$H$_{10}$N$_3$O$_3$P<br>MW = 275.2<br>Cas Number:<br>26386-88-9 | Consumed in Method 2 to form PAA; any unreacted DPPA is removed during isolation of compound (IV).<br>Measured: ≤2.4 ppm in compound (IV),<br>n = 29<br>(LOQ = 0.4 ppm) | Measured: <LOQ<br>n = 6<br>(LOQ = 0.7 ppm) |
| 2 | NBOC-EDA 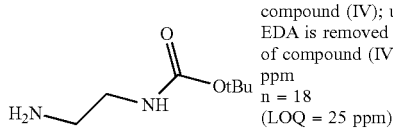 C$_7$H$_{16}$N$_2$O$_2$<br>MW = 160.2<br>CAS Number: 57260-73-8<br>Reagent | Consumed in Method 2 to form compound (IV); unreacted NBOC-EDA is removed during isolation of compound (IV); measured: ≤97 ppm<br>n = 18<br>(LOQ = 25 ppm) | Measured: <LOQ<br>n = 6<br>(LOQ = 10 ppm) |
| 3 | Triethylamine<br>Et$_3$N<br>C$_6$H$_{15}$N | Removed in aqueous washes during Method 2; below WHO limit in Method 2 product.<br>Measured: <100 ppm in compound (IV),<br>n = 29<br>(LOQ = 100 ppm) | Measured: <13.5 ppm,<br>n = 8<br>(LOQ = 13.5 ppm)<br>WHO limit: 320 ppm |

TABLE 11-continued

List of starting materials and structurally related impurities in Method 2

| Entry | Substance | Control/Fate | Measured Levels in Drug Substance |
|---|---|---|---|
| 4 | Diphenyl phosphate<br>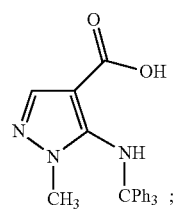 | Removed in aqueous washes during Method 2.<br>Measured: ≤147 ppm in compound (IV),<br>n = 31<br>(LOQ = 5 ppm) | Measured: <LOQ<br>n = 6<br>(LOQ = 10 ppm) |
| 5 | Azide anion<br>$N_3^-$<br>MW = 42.0<br>By-product of DPPA reagent | Removed in aqueous washes during Method 2.<br>Measured: <5 ppm in compound (IV),<br>n = 29<br>(LOQ = 5 ppm) | Measured: <LOQ<br>n = 6<br>(LOQ = 5 ppm) |

Embodiments

1. A method of making compound (IV) comprising the steps of:

(a) forming a mixture comprising diphenylphosphoryl azide and compound (XIV):

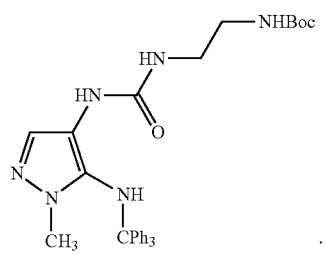

(XIV)

(b) adding a solvent comprising water;
(c) adding NBOC-EDA;
(d) filtering the mixture and collecting a wet cake comprising crude product; and
(e) obtaining compound (IV):

(IV)

2. The method of Embodiment 1, wherein step (a) comprises:

(1) forming a mixture comprising toluene, triethylamine, 1.2 equivalents of diphenylphosphoryl azide, and 1.0 equivalent of compound (XIV) while maintaining the temperature of the mixture below 40° C.;

(2) adjusting the temperature of the mixture to 45° C. and agitating for at least about 1 hour;

(3) adjusting the temperature of the mixture to below 40° C.;

(4) adding 0.2 equivalents of diphenylphosphoryl azide while maintaining the temperature of the mixture below 40° C.; and (5) adjusting the temperature of the mixture to 45° C. and agitating the mixture for at least 1 hour.

3. The method of Embodiment 1, wherein step (b) comprises:

(1) adjusting the temperature of the mixture to 25° C.;
(2) adding the solvent comprising water while maintaining the temperature of the mixture at about 25° C.;
(3) agitating the mixture at 25° C. for at least 10 minutes; and
(4) discarding the lower aqueous phase after phase separation.

4. The method of Embodiment 1, wherein step (b) comprises:

(1) adding the solvent comprising water while maintaining the temperature of the mixture at about 25° C.;
(2) agitating the mixture at 25° C. for at least 10 minutes;
(3) discarding the lower aqueous phase after phase separation;
(4) drying the organic phase by distillation at a temperature less than 40° C.

5. The method of Embodiment 1, wherein step (c) comprises adding NBOC-EDA in two portions.

6. The method of Embodiment 1, wherein step (c) comprises:

(1) adding 5.7 volumes of toluene;
(2) adding 0.19 equivalents of NBOC-EDA;
(3) adjusting the temperature to 90° C.;
(4) adding a further 0.81 equivalents of NBOC-EDA in toluene while maintaining the temperature of the mixture at 90° C.; and
(5) agitating the mixture at 90° C. for 4 to 5 hours.

7. The method of Embodiment 1, wherein step (d) comprises:

(1) adjusting the temperature of the mixture to 30° C.;
(2) agitating the mixture at 30° C. for at least one hour; and
(3) filtering the mixture to collect the wet cake comprising crude product.

8. The method of Embodiment 7, further comprising washing the wet cake with 2.3 volumes of toluene.

9. The method of Embodiment 1, wherein the wet cake comprising crude product is washed with a mixture of dichloromethane and ethanol.

10. The method of Embodiment 1, wherein step (e) comprises:
(1) concentrating the organic phase to 6 to 8 volumes;
(2) adjusting the temperature to 3° C.;
(3) agitating the mixture at 3° C. for at least one hour; and
(4) filtering the reaction mixture to collect a wet cake.

11. The method of Embodiment 10, wherein step (e) further comprises:
(5) washing the wet cake with 1.3 volumes of cold ethanol; and
(6) drying the product under reduced pressure with a nitrogen purge.

12. A method of making compound (XIV):

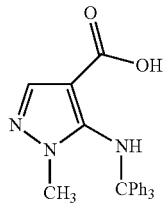

(XIV)

comprising the steps of:
(a) forming a mixture comprising triethylamine and compound (XII):

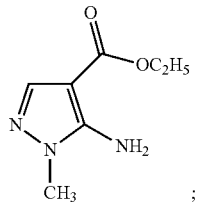

(XII)

(b) adding trityl chloride ($ClCPh_3$) to the mixture of step (a);
(c) adding an aqueous solution comprising sodium hydroxide;
(d) adding an aqueous solution comprising hydrochloric acid;
(e) adding isopropyl acetate and n-heptane; and
(f) obtaining compound (XIV).

13. The method of Embodiment 12, wherein step (a) comprises combining 1.5 equivalents of triethylamine, 1.0 equivalent of compound (XII) and 5.0 volumes of tetrahydrofuran to yield the mixture.

14. The method of Embodiment 12, wherein step (b) comprises:
(1) adding 1.2 equivalents of trityl chloride while maintaining the temperature of the mixture between 20 and 40° C.; and
(2) adjusting the temperature of the mixture to 65° C.; and
(3) agitating the mixture at 65° C. for 11 to 16 hours.

15. The method of Embodiment 12, wherein step (c) comprises:
(1) adjusting the temperature of the mixture to between 25 and 35° C.;
(2) adding the aqueous solution comprising 2.5 equivalents of sodium hydroxide, 0.7 equivalents of water and 4.0 volumes of methanol while maintaining the temperature of the mixture between 25 and 50° C.;

(3) adjusting the temperature to 65° C.; and
(4) agitating the mixture at 65° C. for 11 to 16 hours.

16. The method of Embodiment 12, wherein step (d) comprises:
(1) adjusting the temperature of the mixture to between 0 and 10° C.;
(2) adding the aqueous solution comprising 3.4 volumes of 2N hydrochloric acid to adjust the pH to between 9 and 10 while maintaining the temperature of the mixture between 0 and 10° C.;
(3) adding 6.0 volumes of dichloromethane while maintaining the temperature of the mixture between 0 and 10° C.;
(4) adding the aqueous solution comprising 3.2 volumes of 2N hydrochloric acid to adjust the pH to between 6.5 and 7.5 while maintaining the temperature of the mixture between 0 and 10° C.; and
(5) discarding the aqueous layer after phase separation.

17. The method of Embodiment 12, wherein step (e) comprises:
(1) concentrating the organic layer to 8 to 9 volumes;
(2) adding 5.0 volumes of isopropyl acetate;
(3) concentrating the mixture to 8 to 9 volumes while maintaining the temperature below 40° C.;
(4) adjusting the temperature of the mixture to between 30 and 40° C.; and
(5) adding 9.8 volumes of isopropyl acetate.

18. The method of Embodiment 12, wherein step (f) comprises:
(1) concentrating the mixture to 10 to 12 volumes;
(2) adjusting the temperature to between −10 and 0° C.;
(3) agitating the mixture at between −10 and 0° C. for 2 to 3 hours; and
(4) filtering the reaction mixture to collect a wet cake.

19. The method of Embodiment 18, wherein step (f) further comprises:
(5) forming a slurry with the wet cake and a mixture of 2:1 (v/v) n-heptane:isopropyl acetate 1.3 volumes of cold ethanol; and
(6) drying the product under reduced pressure with heat.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

The invention claimed is:
1. A process of making compound (IV) comprising the steps of:
(a) forming a mixture comprising diphenylphosphoryl azide and compound (XIV):

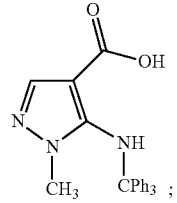

(XIV)

(b) adding a solvent comprising water;
(c) adding NBOC-EDA;
(d) filtering the mixture and collecting a wet cake comprising crude product; and
(e) obtaining compound (IV):

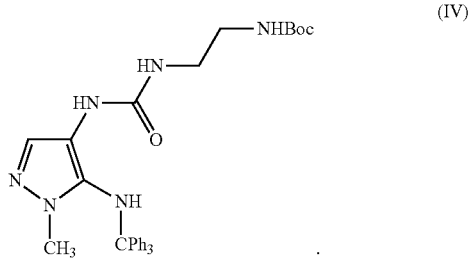

2. The process of claim 1, wherein step (a) comprises:
(1) forming a mixture comprising toluene, triethylamine, 1.2 equivalents of diphenylphosphoryl azide, and 1.0 equivalent of compound (XIV) while maintaining the temperature of the mixture below 40° C.;
(2) adjusting the temperature of the mixture to 45° C. and agitating for at least about 1 hour;
(3) adjusting the temperature of the mixture to below 40° C.;
(4) adding 0.2 equivalents of diphenylphosphoryl azide while maintaining the temperature of the mixture below 40° C.; and
(5) adjusting the temperature of the mixture to 45° C. and agitating the mixture for at least 1 hour.

3. The process of claim 1, wherein step (b) comprises:
(1) adjusting the temperature of the mixture to 25° C.;
(2) adding the solvent comprising water while maintaining the temperature of the mixture at about 25° C.;
(3) agitating the mixture at 25° C. for at least 10 minutes; and
(4) discarding a lower aqueous phase after phase separation.

4. The process of claim 1, wherein step (b) comprises:
(1) adding the solvent comprising water while maintaining the temperature of the mixture at about 25° C.;
(2) agitating the mixture at 25° C. for at least 10 minutes;
(3) discarding the lower aqueous phase after phase separation;
(4) drying an organic phase by distillation at a temperature less than 40° C.

5. The process of claim 1, wherein step (c) comprises adding NBOC-EDA in two portions.

6. The process of claim 1, wherein step (c) comprises:
(1) adding 5.7 volumes of toluene;
(2) adding 0.19 equivalents of NBOC-EDA;
(3) adjusting the temperature to 90° C.;
(4) adding a further 0.81 equivalents of NBOC-EDA in toluene while maintaining the temperature of the mixture at 90° C.; and
(5) agitating the mixture at 90° C. for 4 to 5 hours.

7. The process of claim 1, wherein step (d) comprises:
(1) adjusting the temperature of the mixture to 30° C.;
(2) agitating the mixture at 30° C. for at least one hour; and
(3) filtering the mixture to collect the wet cake comprising crude product.

8. The process of claim 7, further comprising washing the wet cake with 2.3 volumes of toluene.

9. The process of claim 1, wherein the wet cake comprising crude product is washed with a mixture of dichloromethane and ethanol.

10. The process of claim 1, wherein step (e) comprises:
(1) concentrating an organic phase to 6 to 8 volumes;
(2) adjusting the temperature to 3° C.;
(3) agitating the mixture at 3° C. for at least one hour; and
(4) filtering the reaction mixture to collect a wet cake.

11. The process of claim 10, wherein step (e) further comprises:
(1) washing the wet cake with 1.3 volumes of cold ethanol; and
(2) drying the product under reduced pressure with a nitrogen purge.

* * * * *